(12) United States Patent
Manassra

(10) Patent No.: US 9,901,421 B1
(45) Date of Patent: Feb. 27, 2018

(54) ORTHODONTIC BRACES ASSEMBLY

(71) Applicant: Ahmed Manassra, San Jose, CA (US)

(72) Inventor: Ahmed Manassra, San Jose, CA (US)

( * ) Notice: Subject to any disclaimer, the term of this patent is extended or adjusted under 35 U.S.C. 154(b) by 0 days.

(21) Appl. No.: 15/252,922

(22) Filed: Aug. 31, 2016

(51) Int. Cl.
A61C 7/30 (2006.01)
A61C 7/12 (2006.01)

(52) U.S. Cl.
CPC ............... A61C 7/125 (2013.01); A61C 7/30 (2013.01)

(58) Field of Classification Search
CPC ..................................... A61C 7/14; A61C 7/28
See application file for complete search history.

(56) References Cited

U.S. PATENT DOCUMENTS

| 2,908,974 | A | * | 10/1959 | Stifter | A61C 7/12 433/16 |
| 3,946,488 | A | * | 3/1976 | Miller | A61C 7/287 433/11 |
| 4,249,897 | A | * | 2/1981 | Anderson | A61C 7/141 433/16 |
| 4,457,707 | A | | 7/1984 | Smiley et al. | |
| 4,487,581 | A | * | 12/1984 | Adler | A61C 7/30 433/16 |
| RE34,044 | E | | 8/1992 | Broussard | |
| 5,334,015 | A | | 8/1994 | Blechman | |
| D367,116 | S | | 2/1996 | Viazis | |
| 7,431,586 | B1 | | 10/2008 | Silverman | |
| 8,882,498 | B2 | * | 11/2014 | Lewis | A61C 7/14 433/9 |
| 2007/0092849 | A1 | * | 4/2007 | Cosse | A61C 7/14 433/8 |
| 2009/0061380 | A1 | | 3/2009 | Yamamoto | |
| 2012/0132206 | A1 | | 5/2012 | Johnson | |

FOREIGN PATENT DOCUMENTS

| EP | 1226791 | A1 | * | 7/2002 |
| EP | 2431005 | | | 9/2011 |

* cited by examiner

Primary Examiner — Ralph Lewis

(57) ABSTRACT

A orthodontic braces assembly includes a plurality of first clamps. Each of the first clamps is attached to a front surface of an associated one of a plurality of a user's teeth. A plurality of second clamps is provided. Each of the second clamps is removably coupled to an associated one of the first clamps. Each of the second clamps engages a wire thereby facilitating the wire to be extended along the plurality of teeth. Each of the second clamps is removed from the associated first clamp thereby facilitating the teeth to be cleaned.

12 Claims, 7 Drawing Sheets

US 9,901,421 B1

ORTHODONTIC BRACES ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIE THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to braces devices and more particularly pertains to a new braces device for orthodontic bracing of teeth.

BRIEF SUMMARY OF THE INVENTION

An embodiment of the disclosure meets the needs presented above by generally comprising a plurality of first clamps. Each of the first clamps is attached to a front surface of an associated one of a plurality of a user's teeth. A plurality of second clamps is provided. Each of the second clamps is removably coupled to an associated one of the first clamps. Each of the second clamps engages a wire thereby facilitating the wire to be extended along the plurality of teeth. Each of the second clamps is removed from the associated first clamp thereby facilitating the teeth to be cleaned.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
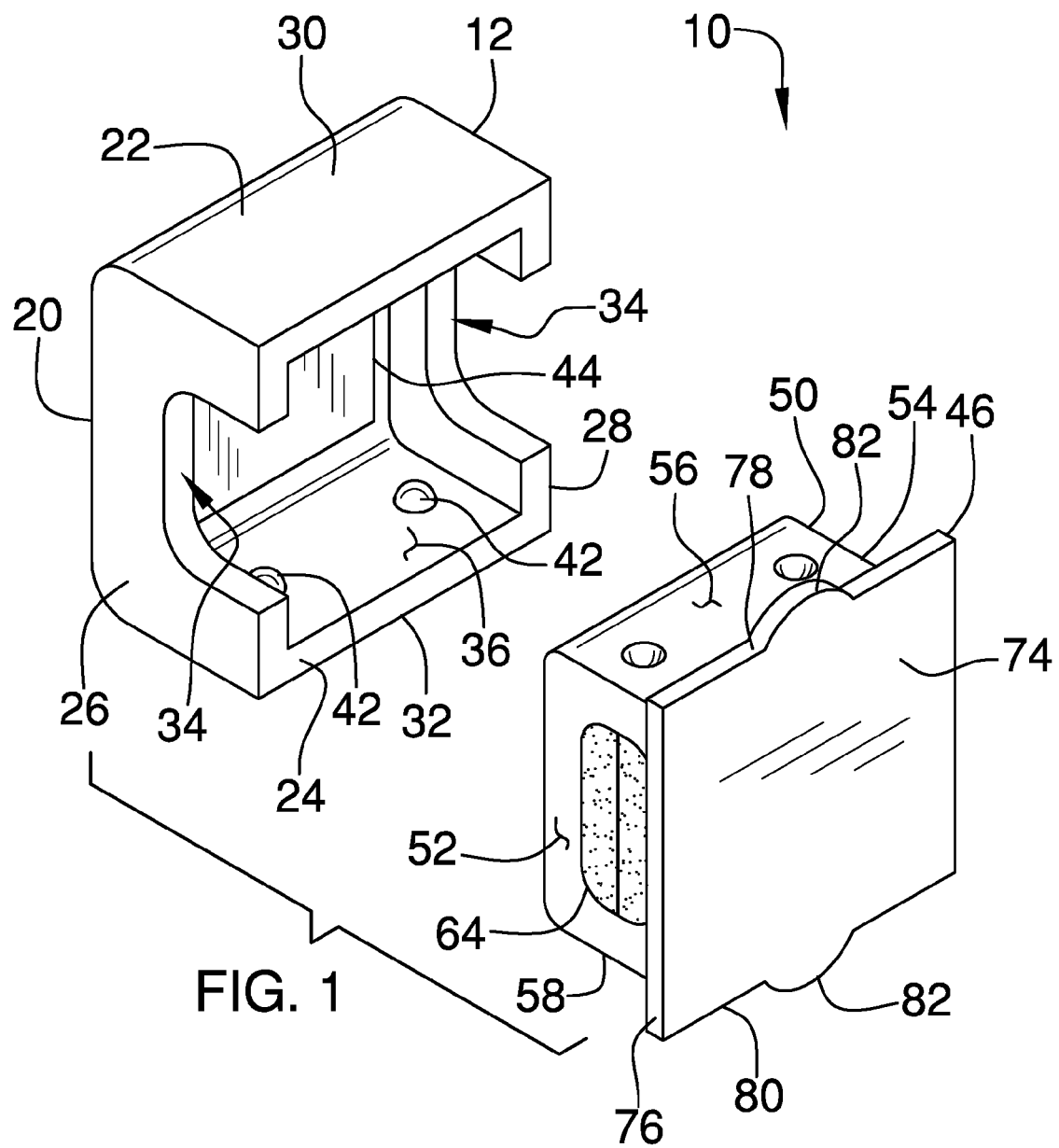
FIG. 1 is a back exploded perspective view of an orthodontic braces assembly according to an embodiment of the disclosure.
Figure 2:
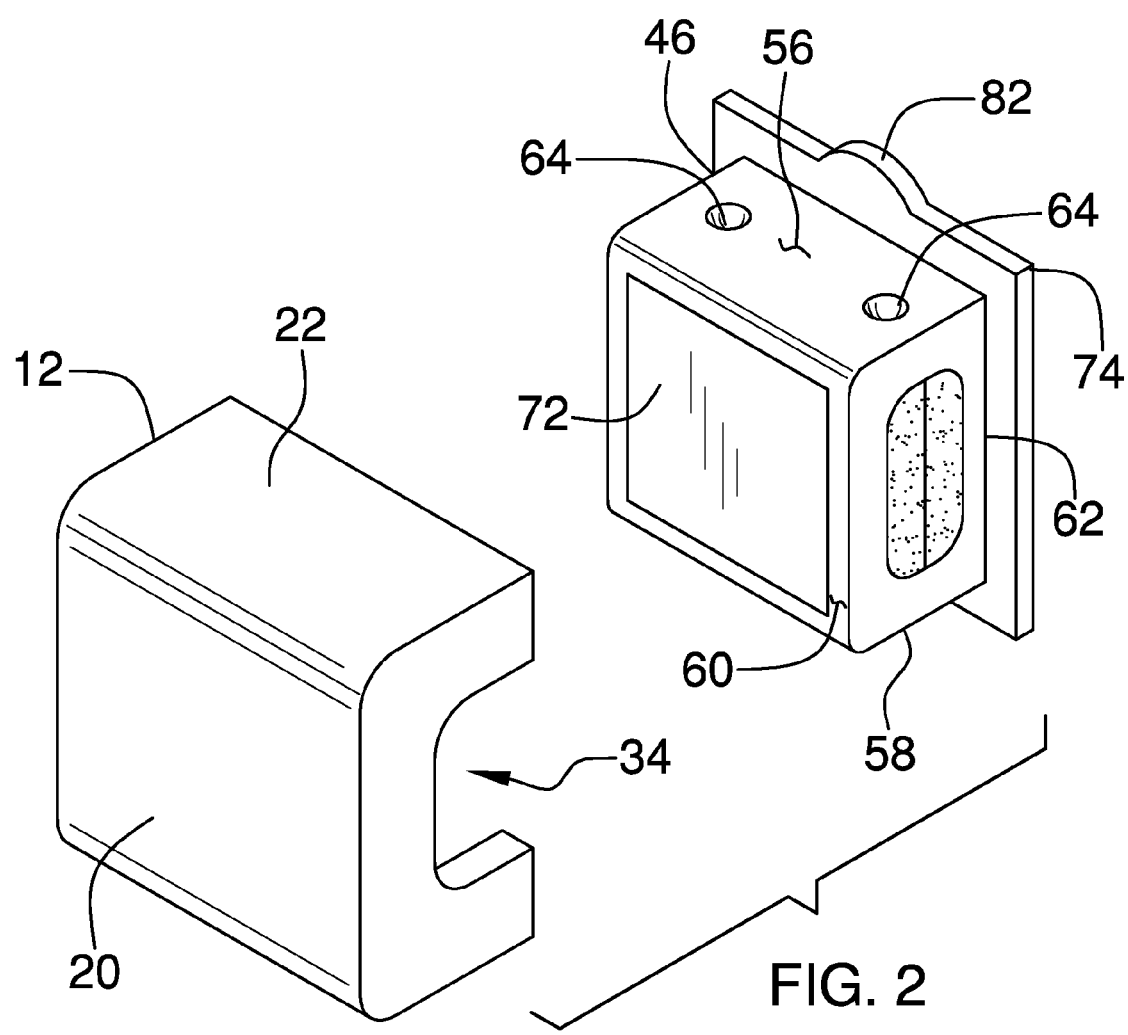
FIG. 2 is a front exploded view of an embodiment of the disclosure.
Figure 3:
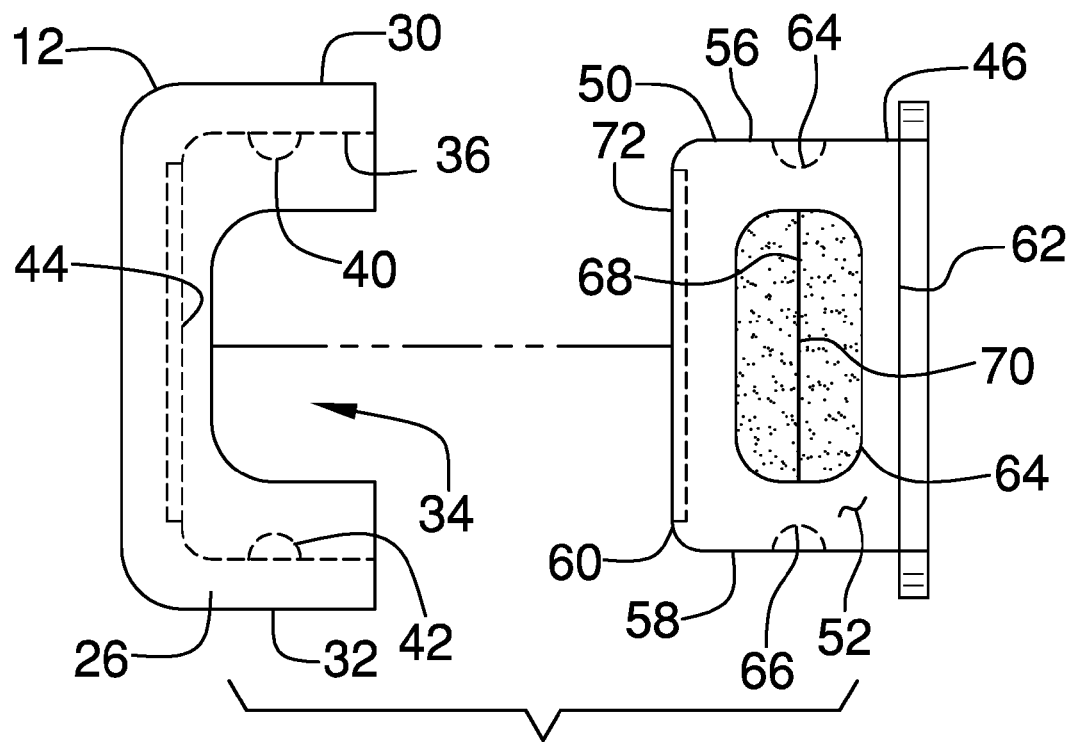
FIG. 3 is a right side phantom view of an embodiment of the disclosure.
Figure 4:
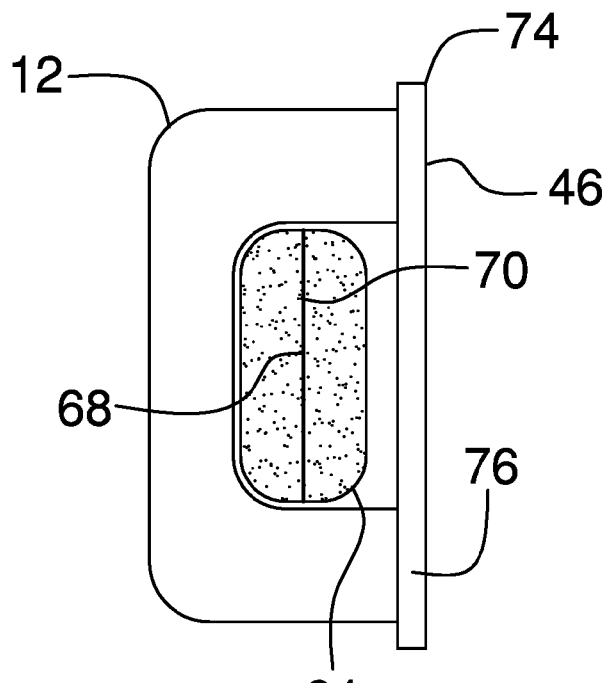
FIG. 4 is a right side view of an embodiment of the disclosure.
Figure 5:
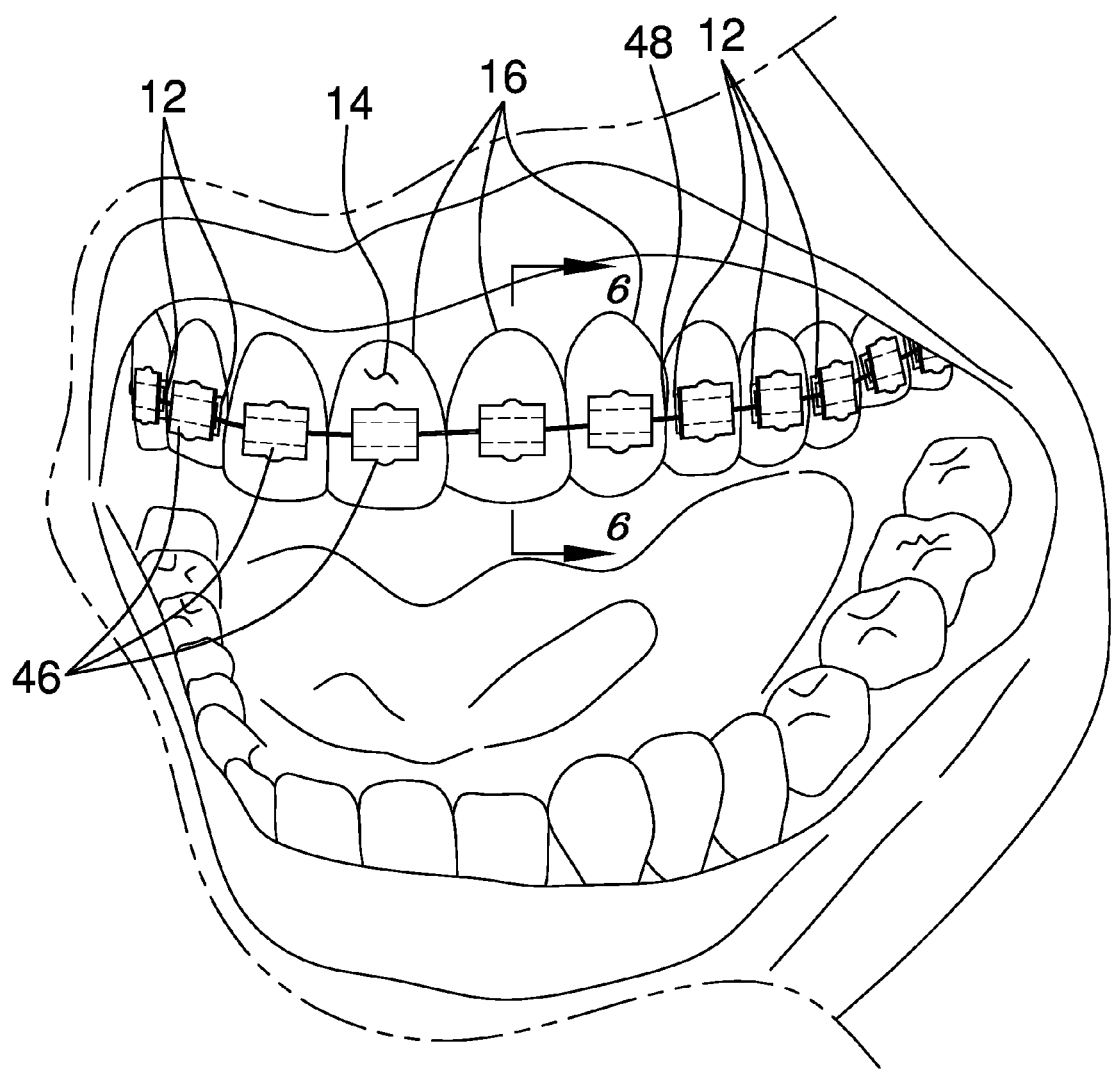
FIG. 5 is a perspective in-use view of an embodiment of the disclosure.
Figure 6:
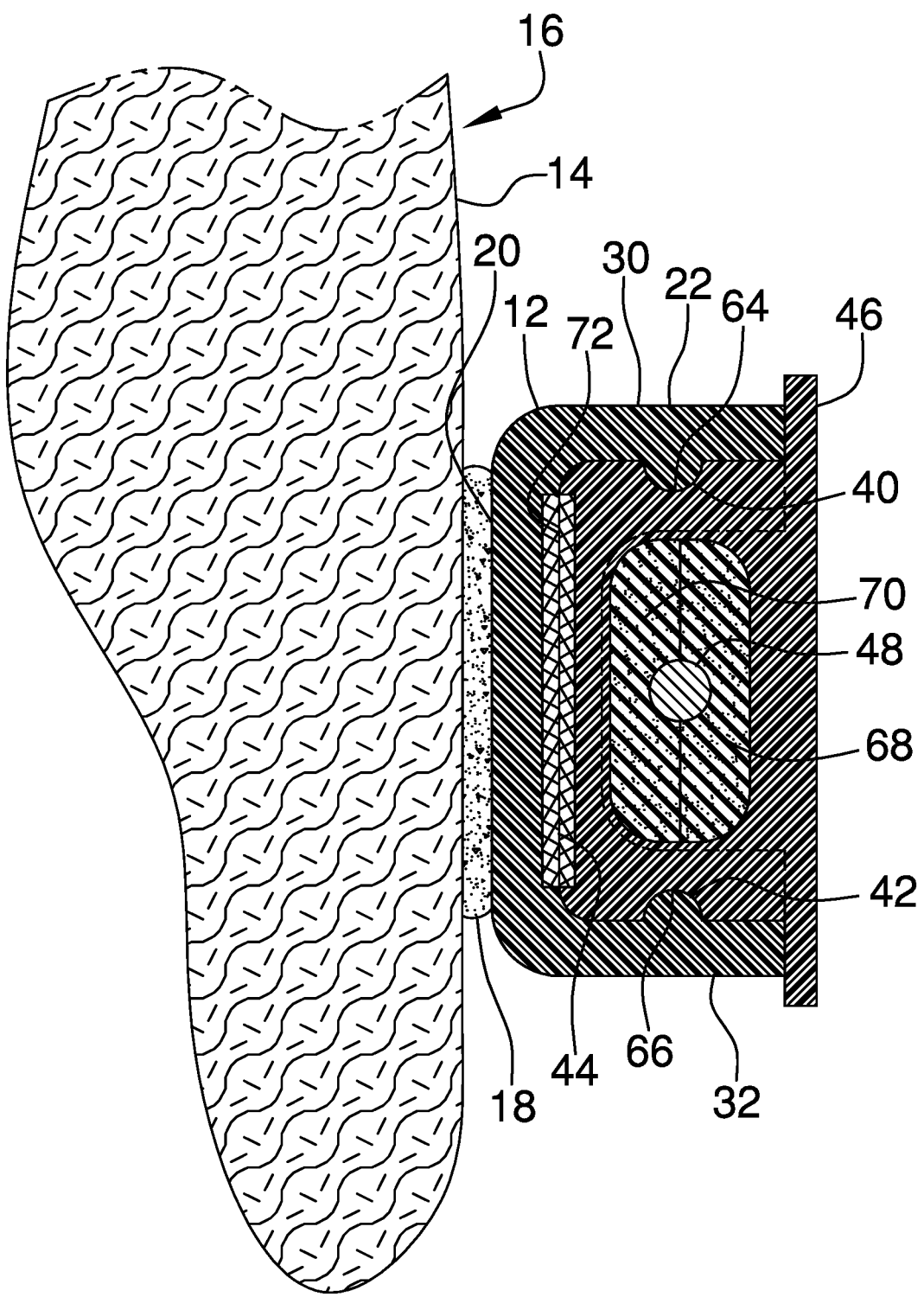
FIG. 6 is a cross sectional view taken along line 6-6 of FIG. 5 of an embodiment of the disclosure.

With reference now to the drawings, and in particular to FIGS. 1 through 8 thereof, a new braces device embodying the principles and concepts of an embodiment of the disclosure and generally designated by the reference numeral 10 will be described.

As best illustrated in FIGS. 1 through 8, the orthodontic braces assembly 10 generally comprises a plurality of first clamps 12. Each of the first clamps 12 is attached to a front surface 14 of an associated one of a plurality of a user's teeth 16. A resin cement 18 may be used to attach each of the first clamps 12 to the associated tooth 16. The resin cement 18 may be a dental cement or the like.

Each of the first clamps 12 comprises a basal wall 20 and a peripheral wall 22 extending away from the basal wall 20. The peripheral wall 22 is coextensive with a perimeter of the basal wall 20. The peripheral wall 22 has a distal edge 24 with respect to the basal wall 20. The peripheral wall 22 has a first lateral side 26, a second lateral side 28, a top side 30 and a bottom side 32.

The peripheral wall 22 has a pair of slots 34. Each of the slots 34 extends from the distal edge 24 toward the basal wall 20. Moreover, each of the slots 34 is positioned on an associated one of the first lateral side 26 and the second lateral side 28. Each of the first clamps 12 has an inner surface 36 and an outer surface 38. The outer surface 38 corresponding to the basal wall 20 is fastened to the front surface 14 of the associated one of the teeth 16.

Each of the first clamps 12 includes a pair of first protrusions 40. Each of the first protrusions 40 extends outwardly from the inner surface 36. Moreover, each of the first protrusions 40 is positioned on the top side 30. The first protrusions 40 are spaced apart from each other.

Each of the first clamps 12 includes a pair of second protrusions 42. Each of the second protrusions 42 extends outwardly from the inner surface 36. Additionally, each of the second protrusions 42 is positioned on the bottom side 32. The second protrusions 42 are spaced apart from each other. A first fastener 44 is provided. The first fastener 44 is recessed into the inner surface 36 corresponding to the basal wall 20. The first fastener 44 may be a magnet.

A plurality of second clamps 46 is provided. Each of the second clamps 46 is removably coupled to an associated one of the first clamps 12. Moreover, each of the second clamps 46 engages a wire 48. Thus, the wire 48 is extended along the plurality of teeth 16. The wire 48 may be an orthodontic braces wire 48 or the like. Each of the second clamps 46 is removed from the associated first clamp 12 to facilitate the teeth 16 to be cleaned.

Each of the second clamps 46 comprises a box 50. The box 50 has a first lateral surface 52, a second lateral surface 54, a top surface 56, a bottom surface 58, a front surface 60 and a back surface 62. The box 50 has an opening 64 extending through the first lateral surface 52 and the second lateral surface 54. The top surface 56 has a pair of first depressions 64 and the bottom surface 58 has a pair of second depressions 66.

The box 50 is inserted into the associated first clamp 12. Each of the first protrusions 40 engages an associated one of the first depressions 64. Each of the second protrusions 42 engages an associated one of the second depressions 66. Thus, the box 50 is removably retained in the associated first clamp 12. The opening 64 is aligned with each of the slots 34 when the box 50 is positioned in the associated first clamp 12. Thus, the wire 48 may be extended through the associated first clamp 12.

A first pad 68 is provided. The first pad 68 is positioned within the opening 64. Moreover, the first pad 68 is coextensive with the opening 64. The first pad 68 may be comprised of a resiliently compressible material.

A second pad 70 is provided. The second pad 70 is positioned within the opening 64. Moreover, the second pad 70 is coextensive with the opening 64. The second pad 70 may be comprised of a resiliently compressible material. The first pad 68 abuts the second pad 70 having the wire 48 compressed therebetween. Thus, the wire 48 is inhibited from moving in the box 50.

A second fastener 72 is provided. The second fastener 72 is recessed into the front surface 60 of the box 50. The second fastener 72 is complementary with respect to the first fastener 44. Thus, the box 50 is removably retained within the associated first clamp 12. The second fastener 72 may comprise a magnet. Thus, the first fastener 44 may magnetically engage the second fastener 72.

A plate 74 is coupled to the back surface 62 of the box 50. The plate 74 has a perimeter edge 76 and the perimeter edge 76 is spaced from the box 50. The perimeter edge 76 has a top side 78 and a bottom side 80. Each of the top side 78 and the bottom side 80 of the plate 74 has a prominence 82. The prominence 82 may be gripped to remove the box 50 from the associated first clamp 12.

Figure 7:
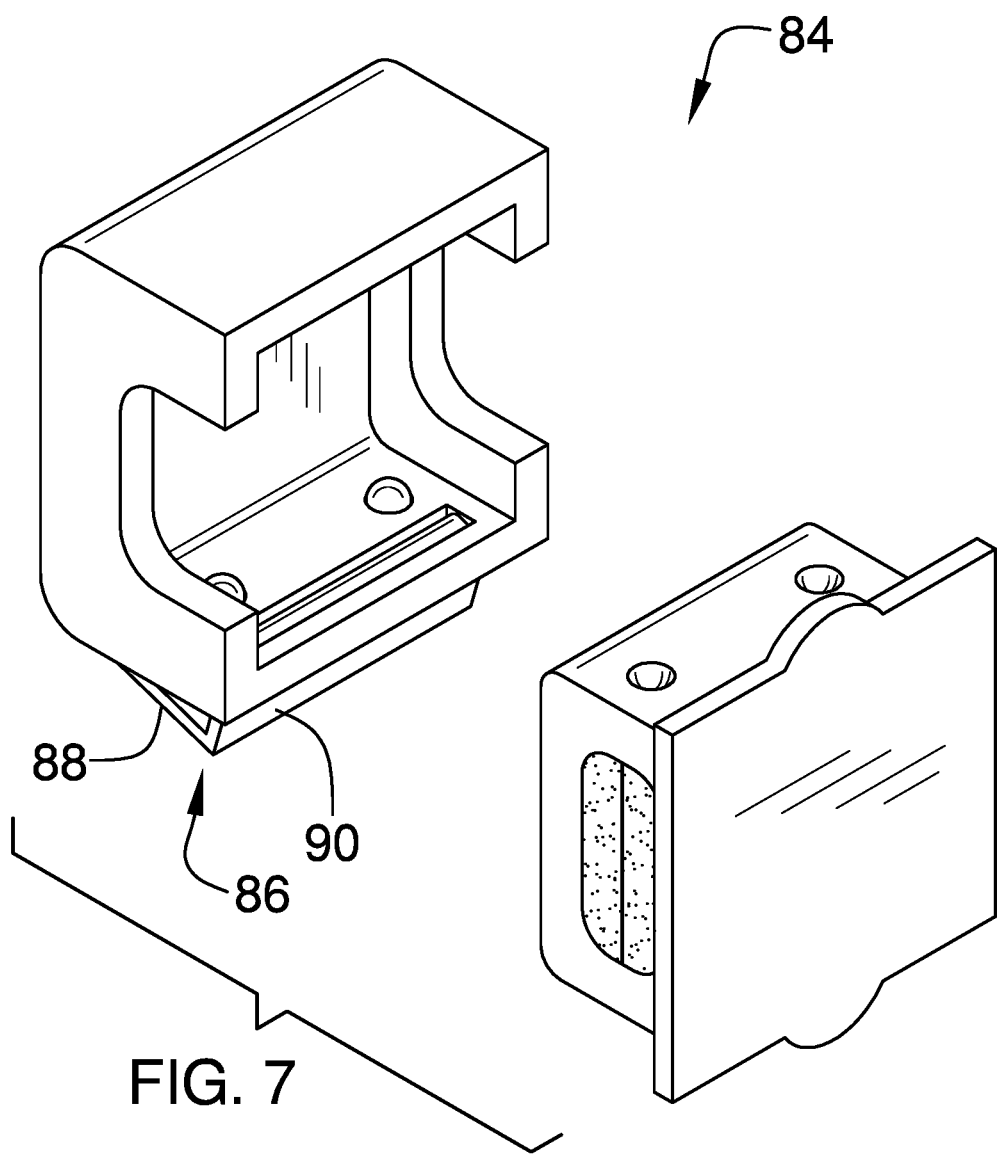
FIG. 7 is a front perspective view of an alternative embodiment of the disclosure.
Figure 8:
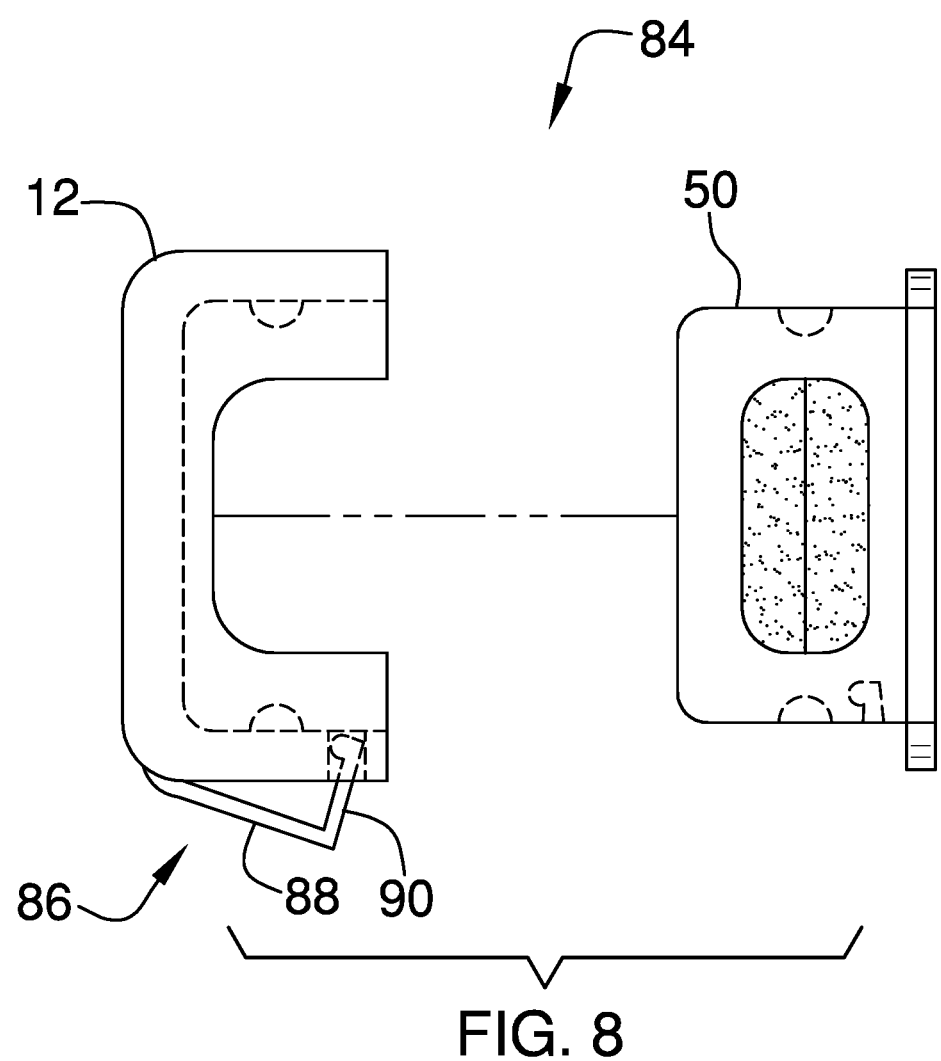
FIG. 8 is an exploded view of an alternative embodiment of the disclosure.

In an alternative embodiment 84 as shown in FIGS. 7 and 8, each of the first clamps 12 may include a lock 86. The lock 86 may comprise a leg 88 and a foot 90. The leg 88 may be hingedly coupled to the bottom side 32 of the first clamp 12. The foot 90 may extend through the bottom side 32. The foot 90 may engage the box 50 when the lock 86 is manipulated into a locking position. Thus, the box 50 is inhibited from being removed from the associated first clamp 12.

In use, each of the first clamps 12 is cement 18ed to the front surface 60 of the associated tooth 16. The wire 48 is extended through the opening 64 in each of the second clamps 46. Each of the second clamps 46 is positioned in the associated first clamp 12. Thus, the wire 48 urges the teeth 16 into a selected position in the convention of orthodontic braces. Each of the second clamps 46 is selectively removed from the associated first clamp 12. Thus, cleaning the front surface 60 of the teeth 16 is enhanced. Each of the second clamps 46 is removed by the user without the need for an orthodontist.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An orthodontic braces assembly being configured to be fixed to teeth, said assembly comprising:
    a plurality of first clamps, each of said first clamps being configured to be attached to a front surface of an associated one of a plurality of a user's teeth, each of said first clamps including a basal wall and a peripheral wall extending away from said basal wall, said peripheral wall being coextensive with a perimeter of said basal wall, said peripheral wall having a distal edge with respect to said basal wall, said peripheral wall having a first lateral side, a second lateral side, a top side and a bottom side, said peripheral wall having a pair of slots, each of said slots extending from said distal edge toward said basal wall, each of said slots being positioned on an associated one of said first lateral side and said second lateral side, each of said first clamps having an inner surface and an outer surface, said outer surface corresponding to said basal wall being configured to be fastened to the front surface of the associated one of the teeth; and
    a plurality of second clamps, each of said second clamps being removably coupled to an associated one of said first clamps, each of said second clamps being configured to engage a wire thereby facilitating the wire to be extended along the plurality of teeth, each of said second clamps being removed from said associated first clamp thereby facilitating the teeth to be cleaned.

2. The assembly according to claim 1, further comprising a pair of first protrusions, each of said first protrusions extending outwardly from said inner surface, each of said first protrusions being positioned on said top wall, said first protrusions being spaced apart from each other.

3. The assembly according to claim 1, further comprising a pair of second protrusions, each of said second protrusions extending outwardly from said inner surface, each of said second protrusions being positioned on said bottom wall, said second protrusions being spaced apart from each other.

4. The assembly according to claim 1, further comprising a first fastener being recessed into said inner surface corresponding to said basal wall.

5. The assembly according to claim 1, wherein each of said second clamps comprises a box having a first lateral surface, a second lateral surface, a top surface, a bottom surface, a front surface and a back surface, said box having an opening extending through said first lateral surface and said second lateral surface, said top surface having a pair of first depressions, said bottom surface having a pair of second depressions.

6. The assembly according to claim 5, wherein:
 each of said first clamps has a pair of first protrusions and a pair of second protrusions; and
 said box is inserted into said associated first clamp having each of said first protrusions engaging an associated one of said first depressions and each of said second protrusions engaging an associated one of said second depressions such that said box is removably retained in said associated first clamp.

7. The assembly according to claim 5, further comprising a first pad being positioned within said opening, said first pad being coextensive with said opening.

8. The assembly according to claim 7, further comprising a second pad being positioned within said opening, said second pad being coextensive with said opening, said first pad abutting said second pad wherein each of said first pad and said second pad is configured to have the wire compressed therebetween.

9. The assembly according to claim 5, further comprising:
 a first fastener; and
 a second fastener being recessed into said front surface of said box, said second fastener being complementary with respect to said first fastener such that said box is removably retained within said associated first clamp.

10. The assembly according to claim 5, further comprising a plate being coupled to said back surface of said box, said plate having a perimeter edge, said perimeter edge being spaced from said box, said perimeter edge having a top side and a bottom side, each of said top side and said bottom side having a prominence wherein said prominence is configured to be gripped thereby facilitating said box to be removed from said associated first clamp.

11. An orthodontic braces assembly being configured to be fixed to teeth, said assembly comprising:
 a plurality of first clamps, each of said first clamps being configured to be attached to a front surface of an associated one of a plurality of a user's teeth; and
 a plurality of second clamps, each of said second clamps being removably coupled to an associated one of said first clamps, each of said second clamps being configured to engage a wire thereby facilitating the wire to be extended along the plurality of teeth, each of said second clamps being removed from said associated first clamp thereby facilitating the teeth to be cleaned, each of said second clamps including a box having a first lateral surface, a second lateral surface, a top surface, a bottom surface, a front surface and a back surface, said box having an opening extending through said first lateral surface and said second lateral surface, said top surface having a pair of first depressions, said bottom surface having a pair of second depressions;
 each of said first clamps having a pair of slots, each of said slots being positioned on an associated one of a first lateral side and a second lateral side of a peripheral wall of said first clamp; and
 said opening is aligned with each of said slots when said box is positioned in said associated first clamp wherein said box is configured to facilitate the wire to extend through said associated first clamp.

12. An orthodontic braces assembly being configured to be fixed to teeth, said assembly comprising:
 a plurality of first clamps, each of said first clamps being configured to be attached to a front surface of an associated one of a plurality of a user's teeth, each of said first clamps comprising:
  a basal wall and a peripheral wall extending away from said basal wall, said peripheral wall being coextensive with a perimeter of said basal wall, said peripheral wall having a distal edge with respect to said basal wall, said peripheral wall having a first lateral side, a second lateral side, a top side and a bottom side, said peripheral wall having a pair of slots, each of said slots extending from said distal edge toward said basal wall, each of said slots being positioned on an associated one of said first lateral side and said second lateral side, each of said first clamps having an inner surface and an outer surface, said outer surface corresponding to said basal wall being configured to be fastened to the front surface of the associated one of the teeth,
  a pair of first protrusions, each of said first protrusions extending outwardly from said inner surface, each of said first protrusions being positioned on said top wall, said first protrusions being spaced apart from each other,
  a pair of second protrusions, each of said second protrusions extending outwardly from said inner surface, each of said second protrusions being positioned on said bottom wall, said second protrusions being spaced apart from each other, and
  a first fastener being recessed into said inner surface corresponding to said basal wall; and
 a plurality of second clamps, each of said second clamps being removably coupled to an associated one of said first clamps, each of said second clamps being configured to engage a wire thereby facilitating the wire to be extended along the plurality of teeth, each of said second clamps being removed from said associated first clamp to clean the teeth, each of said second clamps comprising:
  a box having a first lateral surface, a second lateral surface, a top surface, a bottom surface, a front surface and a back surface, said box having an opening extending through said first lateral surface and said second lateral surface, said top surface having a pair of first depressions, said bottom surface having a pair of second depressions, said box being inserted into said associated first clamp having each of said first protrusions engaging an associated one of said first depressions and each of said second protrusions engaging an associated one of said second depressions such that said box is removably retained in said associated first clamp, said opening being aligned with each of said slots when said box is positioned in said associated first clamp wherein said box is configured to facilitate the wire to extend through said associated first clamp,
  a first pad being positioned within said opening, said first pad being coextensive with said opening,
  a second pad being positioned within said opening, said second pad being coextensive with said opening, said first pad abutting said second pad wherein each of said first pad and said second pad is configured to have the wire compressed therebetween, a second fastener being recessed into said front surface of said box, said second fastener being complementary with respect to said first fastener such that said box is removably retained within said associated first clamp, and a plate being coupled to said back surface of said box, said plate having a perimeter edge, said perimeter edge being spaced from said box, said perimeter edge having a top side and a bottom side, each of said top side and said bottom side having a prominence wherein said prominence is configured to be gripped thereby facilitating said box to be removed from said associated first clamp.

* * * * *